United States Patent
Ohsawa et al.

(10) Patent No.: US 8,343,925 B2
(45) Date of Patent: Jan. 1, 2013

(54) COMPOSITION FOR IMPROVING BRAIN FUNCTION AND METHOD FOR IMPROVING BRAIN FUNCTION

(75) Inventors: Kazuhito Ohsawa, Sagamihara (JP); Naoto Uchida, Sagamihara (JP); Kohji Ohki, Sagamihara (JP)

(73) Assignee: Calpis Co., Ltd., Tokyo (JP)

( * ) Notice: Subject to any disclaimer, the term of this patent is extended or adjusted under 35 U.S.C. 154(b) by 26 days.

(21) Appl. No.: 12/890,174

(22) Filed: Sep. 24, 2010

(65) Prior Publication Data
US 2011/0160140 A1   Jun. 30, 2011

(30) Foreign Application Priority Data
Dec. 28, 2009   (JP) .................................. 2009-297025

(51) Int. Cl.
*A01N 37/18* (2006.01)
*A61K 38/00* (2006.01)

(52) U.S. Cl. ...................... 514/17.5; 514/17.7; 514/21.9

(58) Field of Classification Search .......................... None
See application file for complete search history.

(56) References Cited

U.S. PATENT DOCUMENTS

| | | |
|---|---|---|
| 6,410,685 B1 | 6/2002 | Masuyama et al. |
| 6,994,987 B1 | 2/2006 | Yamamoto et al. |
| 2005/0085422 A1 | 4/2005 | Georgiades |
| 2006/0154871 A1 | 7/2006 | Georgiades |
| 2008/0085299 A1 | 4/2008 | Georgiades |

FOREIGN PATENT DOCUMENTS

| | | |
|---|---|---|
| EP | 1018341 A1 | 7/2000 |
| JP | 03-031298 A | 2/1991 |
| JP | 06-041191 A | 2/1994 |
| JP | 2782153 B2 | 7/1998 |
| JP | 11-100328 A | 4/1999 |
| JP | 2001-064197 A | 3/2001 |
| JP | 2001-136995 A | 5/2001 |
| JP | 3898389 B2 | 3/2007 |
| WO | WO 00/75173 A2 | 12/2000 |
| WO | WO 02/46211 A2 | 6/2002 |
| WO | WO 2006/005757 A2 | 1/2006 |
| WO | WO 2007/079977 A2 | 7/2007 |

OTHER PUBLICATIONS

Schenk, J. Med. Chemistry, 1995, 38(21):4141-54.*
Vickers, Drugs Ageing, 2002, 19(7):487-94.*
Bartus et al. "The Cholinergic Hypothesis of Geriatric Memory Dysfunction", Science, vol. 217, Jul. 30, 1982, pp. 408-417.
Japanese Office Action in Japanese Patent Application No. 2011-119960 dated Jan. 19, 2012, including partial translation.

* cited by examiner

*Primary Examiner* — Olga N Chernyshev
(74) *Attorney, Agent, or Firm* — Birch, Stewart, Kolasch & Birch, LLP

(57) ABSTRACT

The present invention provides a composition which may be ingested orally in a small dose for the purpose of improving brain function, and a method for improving brain function. The present invention is a composition for improving brain function, the composition comprising, as an active ingredient, Xaa-Pro-Pro (wherein Xaa represents Ile, Leu or Ser).

8 Claims, 2 Drawing Sheets

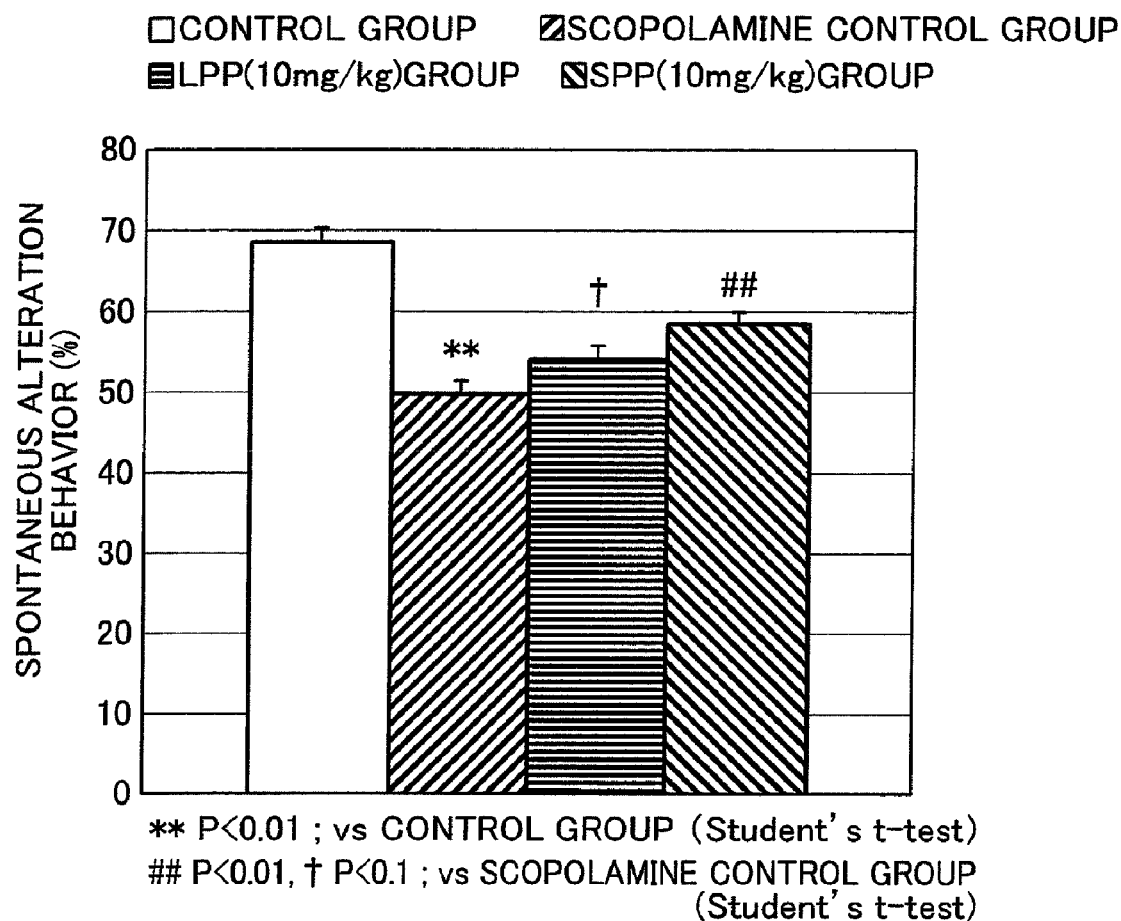

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Synthetic functional peptide
<220> FEATURE:
<221> NAME/KEY: MISC_FEATURE
<222> LOCATION: (1)..(1)
<223> OTHER INFORMATION: Xaa is Leu, Ile, Met, Phe or Trp

<400> SEQUENCE: 1

Xaa Pro Leu Pro Arg
1               5
```

COMPOSITION FOR IMPROVING BRAIN FUNCTION AND METHOD FOR IMPROVING BRAIN FUNCTION

FIELD OF THE INVENTION

The present invention relates to a composition for improving brain function and a method for improving brain function.

BACKGROUND OF THE INVENTION

The symptoms and diseases caused by a deterioration of brain function include depression, schizophrenia, delirium, dementia (cerebrovascular dementia, Alzheimer's disease, and the like), and the like. With the aging of the population in modern society, especially the increase in the number of people with dementia is becoming a serious social issue. There are various symptoms observed among individuals with dementia, and symptoms commonly observed among them include dysmnesia, disorientation, decline in judgment and thinking ability, and the like. The forms of dementia which affect especially a large number of individuals are cerebrovascular dementia and Alzheimer's disease. For example, in patients with cerebrovascular dementia, damage to the nerve cells in the cerebral cortex and hippocampus caused by obstruction of the brain blood flow gives a rise to cognitive impairment and dysmnesia. For this reason, in addition to treating pre-existing diseases, such as high-blood pressure, diabetes, and hypercholesterolemia, which may trigger cerebrovascular disorders, drugs which are capable of improving brain blood flow and/or drugs which are capable of protecting brain nerve cells are administered. In the meantime, causes of Alzheimer's disease have not been clearly elucidated; however, since a decrease in the level of acetylcholine, which is a neurotransmitter in the brain, is observed in the patients with this disease, a hypofunction of cholinergic neurons is assumed to be one of the causes (reference 4). Therefore, a therapeutic strategy aiming at preventing the hypofunction of cholinergic neurons by increasing the concentration of acetylcholine has been the mainstream for the treatment of Alzheimer's disease.

Currently, as a therapeutic drug against Alzheimer's disease, acetylcholinesterase inhibitors, for example, such as donepezil hydrochloride, are commercially available. However, the acetylcholinesterase inhibitors, such as donepezil hydrochloride, have their drawbacks that they should not be administered for an extended period of time due to their hepatotoxicity and strong side-effects as well as that they are costly.

Meantime, as a report in regard to peptides showing an anti-amnesic effect, for example, it has been reported that XPLPR (SEQ ID NO: 1) (X represents L, I, M, F, or W) demonstrated an improving effect against scopolamine-induced amnesia when administered intracerebroventricularly or orally at 300 mg/kg, and, a release of acetylcholine from the intracerebral C3a receptor has been suggested as one of the mechanisms involved in this effect (reference 1). Scopolamine is believed to function as a muscarinic receptor antagonist that induces the hypofunction of cholinergic neurons. Working as an inducer of brain dysfunction, scopolamine is used in the production of model animals to be used in the development of therapeutic drugs against Alzheimer's disease. In regard to the prophylactic and/or curative activities against brain dysfunction by the action of scopolamine, their effects may be demonstrated in behavioral pharmacological tests, such as a Y-shaped maze test, an eight-arm maze test, and a passive avoidance test. Further, the effects of improving and/or strengthening brain function may be demonstrated in the same behavioral pharmacological tests with use of normal animals. However, all these peptides need to be administered in a large dose orally, intraabdominally, intracerebroventricularly, or the like in order to demonstrate their actions; therefore, they are not considered to be orally ingestible substances capable of demonstrating a sufficient level of effects. In addition, there has been no report on evaluation of peptides of the present invention and their analogs; therefore, their actions involved in the improvement of brain function have been hitherto unknown.

Thus, with the progress of the aging of the society, demands for development of pharmaceutical agents, which prevent the symptoms and diseases caused by a deterioration of brain function and further demonstrate curative effects on the symptoms and diseases, and for further development of safer compounds which are excellent in food application are becoming increasingly stronger.

There are several reports about a tripeptide Ile-Pro-Pro (IPP) and homologues thereof. For example, an angiotensin-converting enzyme (ACE) inhibitory agent containing Ile-Pro-Pro as an active ingredient has been known and it was known that Ile-Pro-Pro has an ACE inhibitory activity. A hypotensive lowering activity of Ile-Pro-Pro was also known by oral administration was known and it was reported that fermented milk containing Ile-Pro-Pro has a hypotensive activity (reference 2). Furthermore it has been known that oral administration of Val-Pro-Pro (VPP) and Ile-Pro-Pro (IPP) exhibit inhibitory activities on increase in blood pressure due to cold stress or on decrease in markers of immune function (reference 3). However, no reports evaluated activities of these peptides in improving brain functions and such activities of these peptides can not be expected.

SUMMARY OF THE INVENTION

The present invention provides a composition which may be ingested orally in a small dose for the purpose of improving brain function. Further, the present invention provides a method for improving brain function. Several aspects of the present invention are as follows.

(1) An aspect of the present invention is a composition for improving brain function, the composition comprising, as an active ingredient, Xaa-Pro-Pro (wherein Xaa represents Ile, Leu or Ser) or a salt thereof.

(2) An aspect of the present invention is a composition for improving brain function, the composition comprising, as an active ingredient, Ile-Pro-Pro or a salt thereof.

(3) An aspect of the present invention is a composition for improving brain function, the composition comprising, as an active ingredient, Leu-Pro-Pro or a salt thereof.

(4) An aspect of the present invention is a composition for improving brain function, the composition comprising, as an active ingredient, Ser-Pro-Pro or a salt thereof.

(5) An aspect of the present invention is also the composition described in any one of (1) to (4), which is for oral ingestion.

(6) Especially, an aspect of the present invention is also the composition described in any one of (1) to (5), in which the improving brain function is preventing amnesia.

(7) An aspect of the present invention is also a method for improving brain function, the method including administering to a non-human animal Xaa-Pro-Pro (wherein Xaa represents Ile, Leu or Ser) or a salt thereof.

(8) An aspect of the present invention is also a method for improving brain function, the method comprising administering to a non-human animal Ile-Pro-Pro or a salt thereof.

(9) An aspect of the present invention is also a method for improving brain function, the method comprising administering to a non-human animal Leu-Pro-Pro or a salt thereof.

(10) An aspect of the present invention is also a method for improving brain function, the method comprising administering to a non-human animal Ser-Pro-Pro or a salt thereof.

(11) An aspect of the present invention is also the method described in any one of (7) to (10), in which the administering is oral administration.

(12) Especially, an aspect of the present invention is also the method described in any one of (7) to (11), in which the improving brain function is preventing amnesia.

BRIEF DESCRIPTION OF THE DRAWINGS

FIG. 2 shows a prophylactic effect of reach of peptides Leu-Pro-Pro (LPP) and Ser-Pro-Pro (SPP) against scopolamine-induced amnesia. Water (control), scopolamine alone, or 10 mg/kg weight of Leu-Pro-Pro or 10 mg/kg weight of Ser-Pro-Pro together with scopolamine, was administered to mice, and their respective prophylactic effects against amnesia were evaluated in accordance with a method described in Example 2. The vertical axis in FIG. 2 shows the percentage of spontaneous alternation behavior. In order to confirm whether or not amnesia was induced, a significant difference between a water-administered control group and a scopolamine control group to which scopolamine was administered alone was calculated using Student's t-test.  indicates P<0.01 with respect to the water-administered control group. A significant difference between each of the peptide administered groups and the scopolamine control group was calculated using Student's t-test. ## indicates P<0.01 with respect to the scopolamine alonel group, and † indicates P<0.1 or less.

DESCRIPTION OF THE PREFERRED EMBODIMENTS

Figure 1:
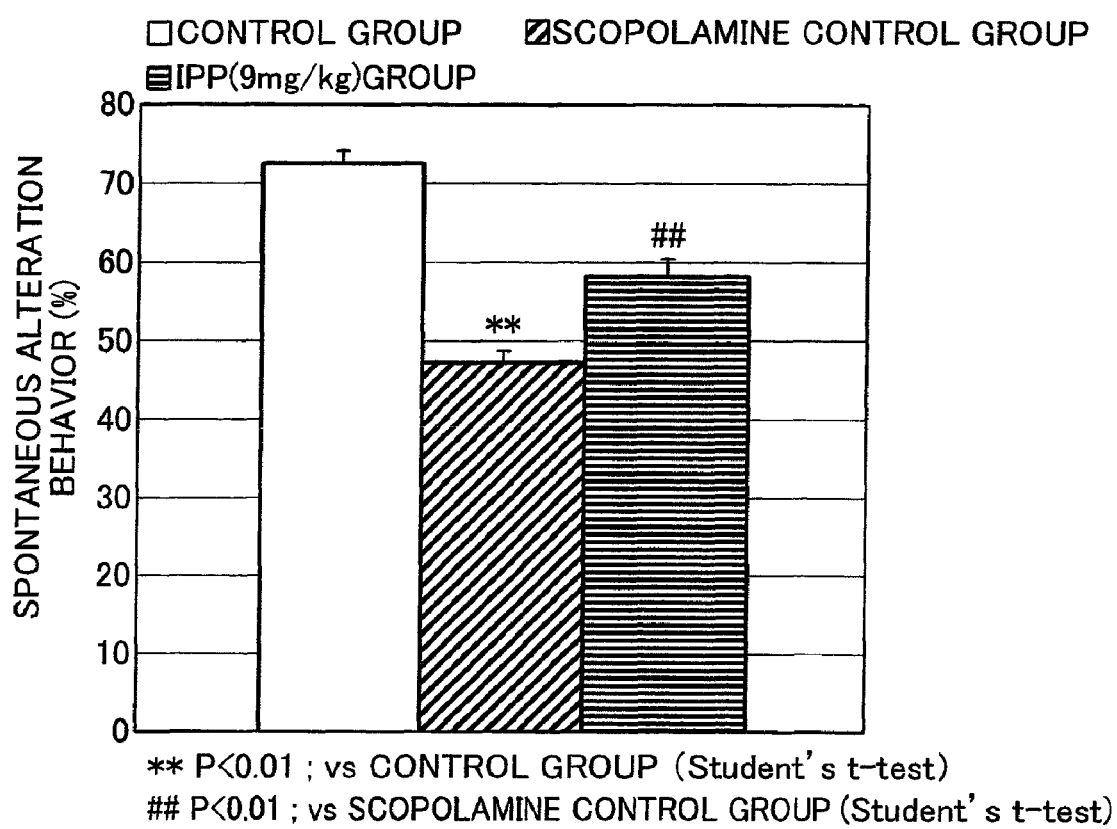
FIG. 1 shows a prophylactic effect of a peptide Ile-Pro-Pro (IPP) against scopolamine-induced amnesia. Water (control), scopolamine alone, or 9.0 mg/kg weight of Ile-Pro-Pro together with scopolamine, was administered to mice, and their respective prophylactic effects against amnesia were evaluated in accordance with a method described in Example 1. The vertical axis in FIG. 1 shows the percentage of spontaneous alternation behavior. In order to confirm whether or not amnesia was induced, a significant difference between a water-administered control group and a scopolamine control group to which scopolamine was administered alone was calculated using Student's t-test.  indicates P<0.01 with respect to the water-administered control group. A significant difference between the IPP-administered group and the scopolamine control group was calculated using Student's t-test. ## indicates P<0.01 with respect to the scopolamine control group

A composition of the present invention includes, as an active ingredient, a peptide Ile-Pro-Pro a peptide Leu-Pro-Pro, or a peptide Ser-Pro-Pro. The peptide Ile-Pro-Pro, the peptide Leu-Pro-Pro, and the peptide Ser-Pro-Pro, which are active ingredients, may be chemically-synthesized peptide or a peptide derived from a natural product. For the chemical synthesis of these peptides, a commonly-used method, such as a solid phase synthesis (t-Boc-chemistry or Fmoc-chemistry) and a liquid phase synthesis, may be employed. For example, these peptides may be synthesized using an automated peptide synthesizer, such as the peptide synthesizer (PSSM-8) available from Shimadzu. A method for the peptide synthesis, appropriate reaction conditions, and the like may be selected based on the common general technical knowledge of a person skilled in the art at the discretion of the person. A method for purifying a chemically-synthesized peptide is also well known to those in the art.

As used in the specification, when referring to the peptide Ile-Pro-Pro, the peptide Leu-Pro-Pro, or the peptide Ser-Pro-Pro, "Ile-Pro-Pro, Leu-Pro-Pro, or Ser-Pro-Pro" or "the peptide Ile-Pro-Pro, the peptide Leu-Pro-Pro, or the peptide Ser-Pro-Pro" include salts thereof unless otherwise clearly indicated or otherwise obvious within the context that they should be excluded. Examples of such salts include salts, such as sodium salts, potassium salts, and hydrochloride salts, which may exist under physiological conditions. Meanwhile, the composition of the present invention may include other peptide and a free amino acid or a salt thereof, in addition to the peptide Ile-Pro-Pro, the peptide Leu-Pro-Pro, or the peptide Ser-Pro-Pro, which is the active ingredient of the composition of the present invention. In relation to the present invention, three-letter codes, single-letter codes, and peptide notation follow the general rules well known to those in the art.

The effect in improving brain function of the composition of the present invention, or the peptide Ile-Pro-Pro, the peptide Leu-Pro-Pro, or the peptide Ser-Pro-Pro may be confirmed using a system based on an evaluation system for therapeutic drugs against Alzheimer's disease, the system using a Y-shaped maze test, for example. Specifically, a muscarinic receptor antagonist, such as scopolamine, may be used on a rat or a mouse so as to cause a hypofunction of the cholinergic neurons. Then, either the rat or the mouse may be administered with a drug, which induces amnesia by causing brain dysfunction, by itself, or the composition of the present invention, the peptide the peptide Ile-Pro-Pro, the peptide Leu-Pro-Pro, or the peptide Ser-Pro-Pro together with such a drug, or the rat or the mouse may be administered, prior to the administration of such a drug, with the composition of the present invention, the peptide Ile-Pro-Pro, the peptide Leu-Pro-Pro, or the peptide Ser-Pro-Pro. Then, the mouse or the rat may be subjected to a test using a Y-shaped maze so that the prophylactic actions against amnesia of the composition of the present invention may be confirmed by using the percentage of change in spontaneous alternation behavior to different arms and the total number of entries into the maze as indicators.

In the tests, the negative control may be, for example, an animal received only water. In an experiment to confirm the prophylactic action against drug-induced amnesia of the peptide Ile-Pro-Pro, the peptide Leu-Pro-Pro, or the peptide Ser-Pro-Pro, an animal administered only with a drug, which induces amnesia by causing brain dysfunction, such as scopolamine, may be included to be used as a control.

The composition of the present invention includes, as an active ingredient, the peptide Ile-Pro-Pro, the peptide Leu-Pro-Pro, or the peptide Ser-Pro-Pro, and oral administration or oral ingestion thereof allows achievement of the desired effects described above. The period of administration or ingestion of the composition of the present invention may be variously adjusted upon consideration of the age of a target of the administration or ingestion, such as a human or non-human animal, and the health conditions and the like of the target. Examples of the non-human animal include non-human higher vertebrate animals, particularly non-human animals, including pet animals, such as dogs and cats, and domestic animals, such as cattle, horses, pigs, and sheep; however, the non-human animal is not limited thereto. A single administration of the composition of the present invention is enough to demonstrate its effects; however, a continuous effect may be expected by continuous ingestion, which is once or more a day. The composition of the present invention when used as medicine may be in the form of drugs for oral administration. For example, the form may be a tablet, a pill, a hard capsule, a soft capsule, a microcapsule, a powder, a granule, a liquid, or the like. When produced as medicine, the composition of the present invention may be produced in a unit dose required for commonly-approved drug administration by, for example, including a pharmaceutically approved material, such as a carrier, an excipient, a filler, an antiseptic, a stabilizer, a binder, a pH modifier, a buffer, a thickener, a gellant, a preservative, and an antioxidant, accordingly as needed.

The composition of the present invention may also be used as a material for food and beverage or a material for animal feed. For example, the composition of the present invention, or the peptide Ile-Pro-Pro, the peptide Leu-Pro-Pro, or the peptide Ser-Pro-Pro, which is the active ingredient of the composition of the present invention, may be considered a functional food, such as a food for specified health use, which is effective in improving brain function.

The dose of administration or ingestion of the present composition, the peptide Ile-Pro-Pro, the peptide Leu-Pro-Pro, or the peptide Ser-Pro-Pro in order obtain desired effects is preferably 0.1 mg/kg weight to 10 mg/kg weight per administration or ingestion in general, in terms of the amount of the peptide Ile-Pro-Pro, the peptide Leu-Pro-Pro, or the peptide Ser-Pro-Pro, which is the active ingredient. The dose per ingestion in a food, which is, for example, a functional food, may also be lowered further than the above-described level, depending on the number of ingestions per day. An appropriate dose of ingestion may be further adjusted upon consideration of various factors as described above.

The nutritional balance, flavors, and the like of a food, such as a functional food, including the composition of the present invention, or the peptide Ile-Pro-Pro, the peptide Leu-Pro-Pro, or the peptide Ser-Pro-Pro, which is the active ingredient of the composition, may be improved by addition of an additive either: made of other ingredient used in food, such as a saccharide, a protein, a lipid, a vitamin, a mineral, and a flavor, which include various carbohydrates, lipids, vitamins, minerals, sweeteners, flavoring agents, coloring agents, texture enhancers, and the like, for example; or made of a mixture thereof. Animal feed containing the composition of the present invention or the peptide Ile-Pro-Pro, the peptide Leu-Pro-Pro, or the peptide Ser-Pro-Pro, which is the active ingredient of the composition, may be prepared similarly to food for human consumption.

For example, the above-described functional food may have the form of a solid, a gel, or a liquid, may be in the form of, for example, any one of various processed foods and beverages, dry powder, a tablet, a capsule, a granule, and the like, and, further, may be any of various beverages, yogurt, a liquid food, jelly, a candy, a retort pouch food, a tablet confectionary, a cookie, a sponge cake, bread, a biscuit, a chocolate, and the like.

When a functional food, such as a food for specified health use, containing the composition of the present invention is manufactured, although depending on how the composition has been added and how the food containing the composition is served as a product, the functional food is prepared so that the amount of the peptide Ile-Pro-Pro, the peptide Leu-Pro-Pro, or the peptide Ser-Pro-Pro, which is the active ingredient of the composition, to be contained in 100 g of the final product may be 1 µg to 10 g, preferably 10 µg to 1 g, more preferably 100 µg to 100 mg.

The composition of the present invention, or the peptide Ile-Pro-Pro, the peptide Leu-Pro-Pro, or the peptide Ser-Pro-Pro, which is the active ingredient of the composition, may improve brain function, thereby being capable of preventing amnesia and strengthen memory. Further, the composition of the present invention or any one of the above-described peptides, which is the active ingredient of the composition, may also be used for treatment or prevention of the symptoms and diseases caused by a deterioration of brain function, the symptoms and diseases including depression, schizophrenia, delirium, dementia (cerebrovascular dementia, Alzheimer's disease, and the like), and the like.

Hereinafter, the present invention will be specifically described by way of Examples; however, the scope of the invention is not limited to Examples.

EXAMPLES

Example 1

Prophylactic Activity of Ile-Pro-Pro Against Amnesia

Male mice (n=15) of the ddY strain (approximately 7-week old) were used, and they took food and water ad lib. Test substances used were 9.0 mg/kg weight of Ile-Pro-Pro. The test substances were administered to the mice once orally 60 minutes before the execution of a Y-shaped maze test for evaluation of spontaneous alternation behavior. Further, 30 minutes before the execution of the Y-shaped maze test, 1 mg/kg weight of scopolamine was subcutaneously administered on the backs of the mice in order to induce brain dysfunction (dysmnesia and/or cognitive impairment) in the mice. In the Y-shaped maze test, a Y-shaped maze was used as an experimental device, in which the length of each arm was 40 cm, the height of the wall was 12 cm, the width of the floor was 3 cm, and the width of the upper part was 10 cm, and three arms were connected to each other at an angle of 120 degrees. Each of the mice was placed at the tip of any one of the arms of the Y-shaped maze, and then let go to freely explore in the maze for 8 minutes. The sequence of the arms each of the mice entered was recorded. The number of entries by each of the mice for each of the arms during the measurement time was counted to be the total number of entries. In the sequence, the combination in which three different arms were selected in succession (for example, with the three arms respectively called A, B, and C, if the sequence of the arms entered is ABCBACACB, the count is 4 inclusive of overlapping) was investigated, and the number of the count was used as the number of spontaneous alternation behavior. The percentage of spontaneous alternation behavior was calculated by dividing the number of spontaneous alternation behavior by a number obtained by subtracting 2 from the total number of entries, and multiplying a resultant number by 100. The percentage of spontaneous alternation behavior was used as an indicator. A higher value of the indicator suggested better maintenance of short-term memory. The measured values were expressed in the form of mean±standard error for each group. A significant difference between the control group and the scopolamine control group was calculated using Student's t-test. Results are shown in FIG. 1. It was suggested that Ile-Pro-Pro had a prophylactic activity against amnesia when administered at a dose of 9.0 mg/kg weight.

Example 2

Prophylactic Activity of Leu-Pro-Pro and Ser-Pro-Pro Against Amnesia

Male mice (n=15) of the ddY strain (approximately 7-week old) were used, and they took food and water ad lib. Test substances used here were: 10 mg/kg weight of Leu-Pro-Pro or 10 mg/kg weight of Ser-Pro-Pro. The test substances were administered to the mice once orally 60 minutes before the execution of a Y-shaped maze test for evaluation of spontaneous alternation behavior. Further, 30 minutes before the execution of the Y-shaped maze test, 1 mg/kg weight of scopolamine was subcutaneously administered on the backs of the mice in order to induce brain dysfunction (dysmnesia and/or cognitive impairment) in the mice. In the Y-shaped maze test, a Y-shaped maze was used as an experimental device, in which the length of each arm was 40 cm, the height of the wall was 12 cm, the width of the floor was 3 cm, and the width of the upper part was 10 cm, and three arms were connected to each other at an angle of 120 degrees. Each of the mice was placed at the tip of any one of the arms of the Y-shaped maze, and then let go to freely explore in the maze for 8 minutes. The arms each of the mice entered were sequentially recorded. The number of entries by each of the mice for each of the arms during the measurement time was counted to be the total number of entries. In the test, the combination in which three distinctive arms were selected in succession was investigated (for example, with the three arms respectively called A, B, and C, if the order of the arms entered is ABCBACACB, the count is 4 inclusive of overlapping), and the number of the count was used as the number of spontaneous alternation behavior. The percentage of spontaneous alternation behavior was calculated by dividing the number of spontaneous alternation behavior by a number obtained by subtracting 2 from the total number of entries, and multiplying a resultant number by 100. The percentage of change in spontaneous alternation behavior was used as an indicator. A higher value of the indicator suggested better maintenance of short-term memory. The measured values were expressed in the form of mean±standard error for each group. A significant difference against the control group was calculated using Student's t-test. Results are shown in FIG. 2. It was suggested that 10 mg/kg weight of Leu-Pro-Pro and 10 mg/kg weight of Ser-Pro-Pro had a prophylactic activity against amnesia.

REFERENCES

1. Japanese Patent No. 3898389
2. Japanese Patent No. 2782153
3. Publication of Japanese Patent Application No. 11-100328
4. Science, 217, 408-417 (1982)

---

---

What is claimed is:

1. A method for preventing amnesia comprising administering to an animal a peptide consisting of the amino acid sequence of Xaa-Pro-Pro or a salt thereof, wherein Xaa represents Ile, Leu or Ser.

2. A method for preventing amnesia comprising administering to an animal a peptide consisting of the amino acid sequence of Ile-Pro-Pro or a salt thereof.

3. A method for preventing amnesia comprising administering to an animal a peptide consisting of the amino acid sequence of Leu-Pro-Pro or a salt thereof.

4. A method for preventing amnesia comprising administering to an animal a peptide consisting of the amino acid sequence of Ser-Pro-Pro or a salt thereof.

5. The method according to any claim 1, wherein the administering is oral administration.

6. The method according to claim 2, wherein the administering is oral administration.

7. The method according to claim 3, wherein the administering is oral administration.

8. The method according to claim 4, wherein the administering is oral administration.

* * * * *